United States Patent [19]

Curtis et al.

[11] Patent Number: 5,681,836
[45] Date of Patent: Oct. 28, 1997

[54] METHANESULFONATE SALTS OF ANTIPSYCHOTIC BENZOFURAN DERIVATIVES

[75] Inventors: Neil Roy Curtis, Puckeridge; Janusz Jozef Kulagowski, Bishops Stortford, both of England; Paul David Leeson, Monmouth Junction, N.J.

[73] Assignee: Merck, Sharp & Dohme, Ltd., Hoddesdon, England

[21] Appl. No.: 727,896

[22] Filed: Oct. 9, 1996

[30] Foreign Application Priority Data

Oct. 18, 1995 [GB] United Kingdom ............... 9521347

[51] Int. Cl.⁶ .................... C07D 405/06; A61K 31/495
[52] U.S. Cl. ................. 514/253; 514/307; 514/320; 514/337; 514/338; 514/414; 544/376; 546/148; 546/196; 546/254.1; 548/454
[58] Field of Search ................... 544/376; 546/148, 546/196, 284.1; 548/454; 514/253, 307, 320, 337, 338, 414

[56] References Cited

FOREIGN PATENT DOCUMENTS

| 077 607 | 4/1983 | European Pat. Off. |
| 281 261 | 9/1988 | European Pat. Off. |
| 43 21 366 A1 | 1/1995 | Germany. |

OTHER PUBLICATIONS

Zagurerskii, et al., Chemical Abstracts, vol. 120, No. 11, ABS. No. 124908t, (1994), "Derivatives of 2–aryl–3–(3–amioethylbenzofuran with neurotropic activity".

Chemical Abstracts, vol. 93, No. 7, ABS. No. 71429c, (1980), Prewysz–Kowinto A., et al., "Synthesis of 3–aminomethyl derivatives of 2–carbethoxy benzofuran".

*Primary Examiner*—Bernard Dentz
*Attorney, Agent, or Firm*—Robert J. North; Melvin Winokur

[57] ABSTRACT

The methanesulfonate salt of a class of antipsychotic compounds comprising a benzo[b]furan moiety and a substituted heterocyclic moiety, linked via the 3-position of the benzo[b]furan moiety by a methylene group, which are antagonists of dopamine receptor subtypes within the brain, being extremely potent antagonists of the human dopamine $D_4$ receptor subtype and having a selective affinity for the $D_4$ subtype over other dopamine receptor subtypes, possess advantageous qualities in terms of their improved aqueous solubility relative to the corresponding free base and, as such, provide for greater ease of formulation and display enhanced pharmacokinetic properties, including oral absorption.

16 Claims, No Drawings

METHANESULFONATE SALTS OF ANTIPSYCHOTIC BENZOFURAN DERIVATIVES

This invention relates to a particular salt form of a discrete class of heteroaromatic compounds. More particularly, the invention is concerned with the methanesulfonate salt of a family of benzofuran derivatives which are antagonists of dopamine receptor subtypes within the brain and are therefore of benefit in the treatment and/or prevention of psychotic disorders such as schizophrenia.

The "dopamine hypothesis" of schizophrenia predicts an increased activity of dopamine neurotransmission in the disease. The hypothesis is supported by early observations that drugs, such as amphetamine, with dopamine agonist or dopamine-releasing properties are capable of eliciting a psychosis indistinguishable from acute paranoid schizophrenia.

Schizophrenia is a disorder which is conventionally treated with drugs known as neuroleptics. In the majority of cases, the symptoms of schizophrenia can be treated successfully with so-called "classical" neuroleptic agents such as haloperidol. Classical neuroleptics generally are antagonists at dopamine $D_2$ receptors. The fact that classical neuroleptic drugs have an action on dopamine receptors in the brain thus lends credence to the "dopamine hypothesis" of schizophrenia.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London), 1991, 350, 610) and $D_5$ (Sunahara et al., Nature (London), 1991, 350, 614) receptor subtypes have been described.

Notwithstanding their beneficial antipsychotic effects, classical neuroleptic agents such as haloperidol are frequently responsible for eliciting acute extrapyramidal symptoms (movement disorders) and neuroendocrine (hormonal) disturbances. These side-effects, which clearly detract from the clinical desirability of classical neuroleptics, are believed to be attributable to $D_2$ receptor blockade in the striatal region of the brain. It is considered (Van Tol et al., supra; and WO-A-92/10571) that compounds which can interact selectively with the dopamine $D_4$ receptor subtype, whilst having a less-pronounced action at the $D_2$ subtype, might be free from, or at any rate less prone to, the side-effects associated with classical neuroleptics, whilst at the same time maintaining a beneficial level of antipsychotic activity.

The methanesulfonate salts in accordance with the present invention, being antagonists of dopamine receptor subtypes within the brain, are accordingly of benefit in the treatment and/or prevention of psychotic disorders such as schizophrenia. In particular, the salts according to the invention are extremely potent antagonists of the human dopamine $D_4$ receptor subtype. Moreover, the salts of this invention have a selective affinity for the dopamine $D_4$ receptor subtype over other dopamine receptor subtypes, in particular the $D_2$ subtype, and can therefore be expected to manifest fewer side-effects than those associated with classical neuroleptic drugs.

The methanesulfonate salts in accordance with the present invention have been found to possess advantageous qualities in terms of their improved aqueous solubility relative to the corresponding free base. As such, the salts of this invention provide for greater ease of formulation and display enhanced pharmacokinetic properties, including oral absorption.

Co-pending International Patent Application No. PCT/GB95/00947, published on 9 Nov. 1995 as WO 95/29911, describes a class of substituted benzofuran derivatives which are antagonists of dopamine receptor subtypes within the brain, being extremely potent antagonists of the human dopamine $D_4$ receptor subtype and having a selective affinity for the $D_4$ subtype over other dopamine receptor subtypes, in particular the $D_2$ subtype. These compounds are stated therein to be of benefit in the treatment and/or prevention of psychotic disorders such as schizophrenia whilst manifesting fewer side-effects than those associated with classical neuroleptic drugs.

EP-A-0077607 describes a class of piperidine derivatives substituted in the 3-position by a substituted phenyl moiety and on the ring nitrogen atom by inter alia an optionally substituted benzofuryl or benzofuryl-alkyl group. Certain of these compounds are stated to be dopamine agonists, whilst others are alleged to be dopamine antagonists. There is, however, no disclosure in EP-A-0077607 of substitution at the 4-position of the piperidine ring, nor is there any suggestion that the compounds described therein might be potent antagonists of the human dopamine $D_4$ receptor subtype, still less that they might have a selective affinity for the dopamine $D_4$ receptor subtype over other dopamine receptor subtypes, and especially the $D_2$ subtype.

The present invention provides the methanesulfonate (mesylate) salt of a compound of formula I:

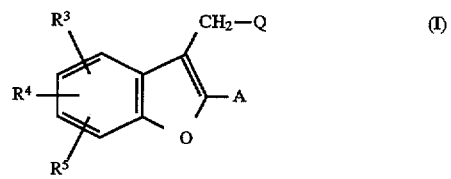

wherein

A represents hydrogen, $C_{1-6}$ alkyl, $C_{1-6}$ alkoxy, halogen, cyano or trifluoromethyl;

Q represents a moiety of formula Qa, Qb, Qc or Qd:

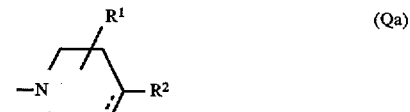

(Qa)

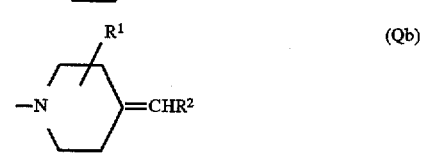

(Qb)

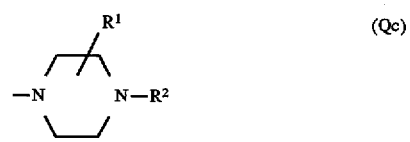

(Qc)

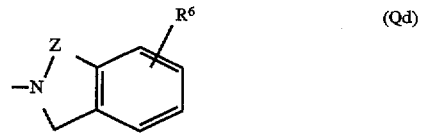

(Qd)

in which the broken line represents an optional chemical bond;

$R^1$ represents hydrogen, or an optionally substituted $C_{1-6}$ alkyl, $C_{1-6}$ alkoxy, $C_{2-6}$ alkenyl, $C_{2-6}$ alkynyl, aryl, aryl$(C_{1-6})$alkyl, aryl$(C_{1-6})$alkoxy, aryl$(C_{2-6})$alkenyl, aryl$(C_{2-6})$alkynyl, $C_{3-7}$ heterocycloalkyl$(C_{1-6})$alkyl, heteroaryl, heteroaryl$(C_{1-6})$alkyl, heteroaryl$(C_{2-6})$alkenyl or heteroaryl$(C_{2-6})$alkynyl group;

$R^2$ represents an optionally substituted $C_{1-6}$ alkyl, $C_{1-6}$ alkoxy, $C_{2-6}$ alkenyl, $C_{2-6}$ alkynyl, aryl, aryl$(C_{1-6})$alkyl, aryloxy$(C_{1-6})$alkyl, aryl$(C_{1-6})$alkoxy, aryl$(C_{2-6})$alkenyl, aryl$(C_{2-6})$alkynyl, $C_{3-7}$ heterocycloalkyl$(C_{1-6})$alkyl, heteroaryl, heteroaryl$(C_{1-6})$alkyl, heteroaryl$(C_{2-6})$alkenyl or heteroaryl$(C_{2-6})$alkynyl group;

$R^3$, $R^4$ and $R^5$ independently represent hydrogen, hydrocarbon, a heterocyclic group, halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$ or $-CONR^aR^b$;

Z represents $-CH_2-$ or $-CH_2CH_2-$;

$R^6$ represents hydrogen or halogen, or an optionally substituted $C_{1-6}$ alkyl, $C_{1-6}$ alkoxy, aryl, aryloxy, aryl$(C_{1-6})$ alkyl, aryl$(C_{1-6})$alkoxy or heteroaryl group; and $R^a$ and $R^b$ independently represent hydrogen, hydrocarbon or a heterocyclic group.

Pharmaceutically acceptable salts of the compounds of formula I above are generically encompassed within the scope of co-pending International Patent Application No. PCT/GB95/00947, published on 9 Nov. 1995 as WO 95/29911. Furthermore, the hydrochloride salts of three separate compounds of formula I above are specifically disclosed therein. There is, however, no specific disclosure anywhere in that co-pending application of the methanesulfonate salt of a compound of formula I as defined above.

As will be appreciated, the methanesulfonate salts of the compounds of formula I above alleviate the symptoms of schizophrenia, but do not cause sedation or extrapyramidal disorders at the dose thereof which is therapeutically effective in alleviating the symptoms of schizophrenia.

In order to elicit their advantageous properties, the salts according to the present invention ideally have a human dopamine $D_4$ receptor subtype binding affinity ($K_i$) of 10 nM or less, preferably 2 nM or less; and at least a 50-fold, suitably at least a 70-fold, preferably at least a 100-fold, more preferably at least a 250-fold, and most preferably at least a 500-fold, selective affinity for the $D_4$ subtype relative to the $D_2$ subtype.

As will be appreciated, the methanesulfonate salts of the compounds of formula I above are pharmaceutically acceptable salts. Other salts, whether or not pharmaceutically acceptable salts, may be useful in the preparation of the methanesulfonate salts according to the invention. Such salts will suitably include acid addition salts and will, for example, be salts of the compounds of formula I above formed with hydrochloric acid, sulfuric acid, fumaric acid, maleic acid, succinic acid, acetic acid, benzoic acid, oxalic acid, citric acid, tartaric acid, carbonic acid or phosphoric acid.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl$(C_{1-6})$alkyl, aryl, aryl$(C_{1-6})$ alkyl, aryl$(C_{2-6})$alkenyl and aryl$(C_{2-6})$alkynyl.

The expression "a heterocyclic group" as used herein includes cyclic groups containing up to 18 carbon atoms and at least one heteroatom preferably selected from oxygen, nitrogen and sulfur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl$(C_{1-6})$alkyl, heteroaryl, heteroaryl$(C_{1-6})$alkyl, heteroaryl$(C_{2-6})$alkenyl and heteroaryl$(C_{2-6})$ alkynyl groups.

Suitable alkyl groups within the scope of the term "hydrocarbon" and within the definition of the substituents A, $R^1$, $R^2$ and $R^6$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and tert-butyl.

Suitable alkenyl groups within the scope of the term "hydrocarbon" and within the definition of the substituents $R^1$ and $R^2$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^1$ and $R^2$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents $R^1$, $R^2$ and $R^6$ include phenyl and naphthyl.

Particular aryl$(C_{1-6})$alkyl groups within the scope of the term "hydrocarbon" and within the definition of the substituents $R^1$, $R^2$ and $R^6$ include benzyl, naphthylmethyl, phenethyl and phenylpropyl.

A particular aryl$(C_{2-6})$alkenyl group within the scope of the term "hydrocarbon" and within the definition of the substituents $R^1$ and $R^2$ is phenylethenyl.

A particular aryl$(C_{2-6})$alkynyl group within the scope of the term "hydrocarbon" and within the definition of the substituents $R^1$ and $R^2$ is phenylethynyl.

Suitable heterocycloalkyl groups include azetidinyl, pyrrolidinyl, piperidinyl, piperazinyl, morpholinyl and tetrahydrofuryl groups.

A particular $C_{3-7}$ heterocycloalkyl$(C_{1-6})$alkyl group within the scope of the expression "a heterocyclic group" and within the definition of the substituents $R^1$ and $R^2$ is tetrahydrofurylethyl.

Suitable heteroaryl groups within the scope of the expression "a heterocyclic group" and within the definition of the substituents $R^1$, $R^2$ and $R^6$ include pyridinyl, quinolinyl, isoquinolinyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl$(C_{1-6})$alkyl groups within the scope of the expression "a heterocyclic group" and within the definition of the substituents $R^1$ and $R^2$ include thienylmethyl, pyridinylmethyl, pyrimidinylmethyl and pyrazinylmethyl.

The hydrocarbon and heterocyclic groups, as well as the substituents $R^1$, $R^2$ and $R^6$, may in turn be optionally substituted by one or more groups selected from $C_{1-6}$ alkyl, adamantyl, phenyl, aryl$(C_{1-6})$alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl$(C_{1-6})$alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulfinyl, $C_{1-6}$ alkylsulfonyl, arylsulfonyl, trifluoromethane-sulfonyloxy, —NR'R'", —NR'COR'", —NR'CO$_2$R'", —NR'SO$_2$R'", —CH$_2$NR'SO$_2$R'", —NHCONR'R'", —PO(OR')(OR'"), —CONR'R'", —SO$_2$NR'R'" and —CH$_2$SO$_2$NR'R'", in which R' and R'" independently represent hydrogen, $C_{1-6}$ alkyl, aryl or aryl($C_{1-6}$)alkyl.

The term "halogen" as used herein includes fluorine, chlorine, bromine and iodine, especially fluorine and chlorine.

Where the compounds of formula I above have at least one asymmetric centre, they may accordingly exist as enantiomers. Where the compounds of formula I above possess two or more asymmetric centres, they may additionally exist as diastereoisomers. It is to be understood that the methanesulfonate salts of all such isomers of the compounds of formula I and mixtures thereof in any proportion are encompassed within the scope of the present invention.

Suitably, the substituent A represents hydrogen or $C_{1-6}$ alkyl, particularly hydrogen or methyl, and especially hydrogen.

Suitably, the substituent $R^1$ represents hydrogen.

Typical values for the substituent $R^2$ include $C_{1-6}$ alkyl, aryl, aryl($C_{1-6}$)alkyl, aryloxy($C_{1-6}$)alkyl, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl and heteroaryl($C_{2-6}$)alkenyl, any of which groups may be optionally substituted. Suitably, $R^2$ is selected from aryl, aryl($C_{2-6}$)alkenyl, aryl ($C_{2-6}$)alkynyl and heteroaryl, any of which groups may be optionally substituted. Examples of optional substituents on the group $R^2$ include $C_{1-6}$ alkyl, halogen, $C_{1-6}$ alkoxy, $C_{1-3}$ alkylenedioxy, nitro, cyano, aryloxy and arylcarbonyloxy.

Particular values of $R^2$ include methyl, benzoyloxymethyl, ethyl, n-propyl, isopropyl, phenyl, chlorophenyl, ethylphenyl, methoxyphenyl, nitrophenyl, naphthyl, benzyl, chlorobenzyl, phenethyl, phenoxy-methyl, phenylethenyl, fluoro-phenylethenyl, chloro-phenylethenyl, methoxy-phenylethenyl, cyano-phenylethenyl, methylenedioxy-phenylethenyl, phenylethynyl, fluoro-phenylethynyl, tetrahydrofuryl-ethyl, indolyl, benzofuryl, benzthienyl, furylethyl, methyl-furylethyl, thienylethenyl and methyl-furylethenyl.

More particularly, $R^2$ may represent phenyl, methoxyphenyl, phenylethenyl, fluoro-phenylethenyl, chloro-phenylethenyl, cyano-phenylethenyl, methylenedioxy-phenylethenyl, phenylethynyl, fluoro-phenylethynyl or benzofuryl. A specific value for $R^2$ is phenylethenyl, in particular in the (E) geometrical isomeric form.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, methyl, methoxy and benzyloxy, especially hydrogen, fluoro and methoxy, and specifically hydrogen.

Particular values of $R^6$ include hydrogen, methoxy, phenyl, chlorophenyl, phenoxy, benzyloxy, thienyl, chloro and bromo, especially hydrogen.

One sub-class of compounds according to the invention is represented by the methanesulfonate salt of the compounds of formula IIA:

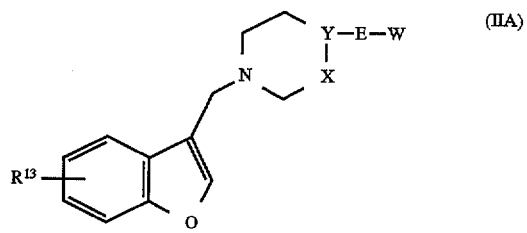

wherein

E represents —(CH$_2$)$_n$—, —CH=CH— or —C≡C—;

n is zero, 1, 2 or 3;

—X—Y— represents —CH$_2$—CH—, —CH=C— or —CH$_2$N—;

W represents a group of formula (i), (ii), (iii), (iv), (v) or (vi):

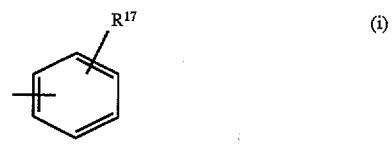

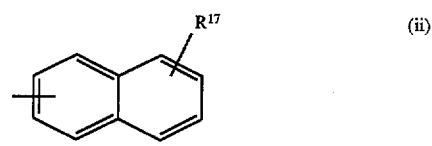

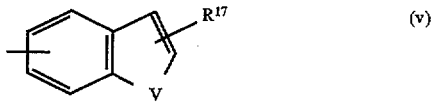

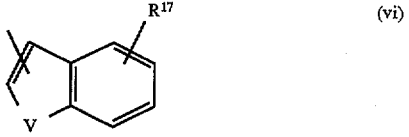

in which V represents oxygen, sulfur or NH; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl.

Particular values of $R^{13}$ include hydrogen, fluoro, chloro, methyl, ethyl, methoxy and benzyloxy, especially hydrogen.

Particular values of $R^{17}$ include hydrogen, fluoro, chloro, cyano, methyl, methoxy and nitro, especially hydrogen.

In one aspect of the compounds of formula IIA, E represents —CH=CH—, —X—Y— represents —CH=C—, W represents a group of formula (i), and $R^{13}$ and $R^{17}$ are both hydrogen. In this aspect, the moiety E is preferably in the (E) geometrical isomeric configuration.

Another sub-class of compounds according to the invention is represented by the methanesulfonate salt of the compounds of formula IIB:

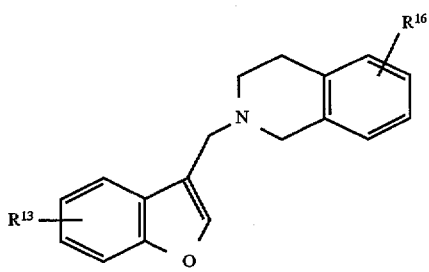

wherein $R^{13}$ is as defined with reference to formula IIA above; and $R^{16}$ represents hydrogen, halogen, $C_{1-6}$ alkyl, $C_{1-6}$ alkoxy, aryl, haloaryl, aryloxy, aryl($C_{1-6}$)alkyl, aryl($C_{1-6}$) alkoxy or heteroaryl.

Particular values of $R^{16}$ include hydrogen, methoxy, phenyl, chlorophenyl, phenoxy, benzyloxy, thienyl, chloro and bromo.

Specific compounds within the scope of the present invention include the methanesulfonate salt of (E)-3-[4-(2-phenylethenyl)-1,2,3,6-tetrahydropyridin-1-yl]methylbenzo[b]furan.

The invention also provides pharmaceutical compositions comprising a methanesulfonate salt in accordance with this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration. An erodible polymer containing the active ingredient may be envisaged. For preparing solid compositions such as tablets, the methanesulfonate salt according to the invention is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a methanesulfonate salt according to the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the methanesulfonate salt according to the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The salt may be administered on a regimen of 1 to 4 times per day.

In order to alleviate the symptoms of schizophrenia without causing sedation or extrapyramidal side-effects, the dosage level of the methanesulfonate salt according to the invention is ideally selected such that the dose administered is effective in substantially completely blocking the dopamine $D_4$ receptor subtype in human brain whilst displaying no or negligible dopamine $D_2$ receptor subtype occupancy. A suitable dosage level in this regard is about 0.001 to 5.0 mg/kg per day, more particularly about 0.005 to 1.0 mg/kg per day, and especially about 0.01 to 0.5 mg/kg per day.

If desired, the methanesulfonate salt according to this invention may be co-administered with another anti-schizophrenic medicament, for example one producing its effects via $D_2$ and/or $5-HT_2$ receptor blockade. In such circumstances, an enhanced anti-schizophrenic effect may be envisaged without a corresponding increase in side-effects such as those caused by, for example, $D_2$ receptor subtype blockade; or a comparable anti-schizophrenic effect with reduced side-effects may alternatively be envisaged. Such co-administration may be desirable where a patient is already established on an anti-schizophrenic treatment regime involving conventional anti-schizophrenic medicaments such as haloperidol or chlorpromazine.

The methanesulfonate salts in accordance with the present invention may be prepared by a process which comprises reacting a compound of formula I as defined above with a substantially equimolar quantity of methanesulfonic acid.

The process is conveniently carried out by stirring the reactants at room temperature in a suitable solvent, for example ethyl acetate; followed by recrystallization from an appropriate solvent, typically a lower alkanol such as 2-propanol.

The methanesulfonate salts according to the present invention may also be prepared by salt exchange, which comprises treating a salt of a compound of formula I as defined above, other than the methanesulfonate salt, with a suitable methanesulfonate (mesylate) salt.

Examples of appropriate mesylate salts which may be utilised in the above salt exchange procedure include metal mesylates, such as sodium mesylate or silver mesylate, and mesylated ion exchange resins.

The compounds of formula I above may be prepared by reacting a compound of formula III with a compound of formula IV:

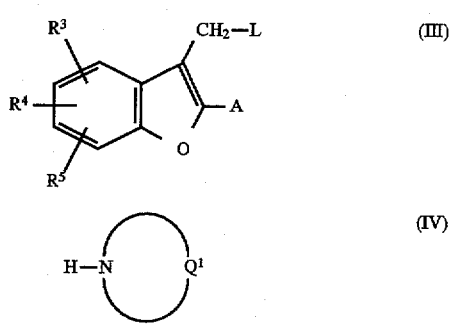

wherein A, $R^3$, $R^4$ and $R^5$ are as defined above, $Q^1$ represents the residue of a moiety of formula Qa to Qd as defined above, and L represents a suitable leaving group.

The leaving group L is suitably a halogen atom, e.g. chlorine or bromine.

The reaction is conveniently carried out by stirring the reactants under basic conditions in a suitable solvent, for example potassium carbonate in N,N-dimethylformamide, or triethylamine in tetrahydrofuran or acetonitrile.

In an alternative procedure, the compounds of formula I above may be prepared by reducing a compound of formula V:

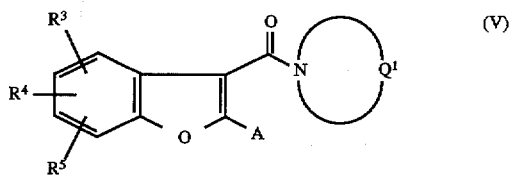

wherein A, $R^3$, $R^4$, $R^5$ and $Q^1$ are as defined above.

The reaction is conveniently carried out by treating compound V with a suitable reducing agent, typically lithium aluminium hydride, in an appropriate solvent, e.g. tetrahydrofuran.

The preparation of the intermediates of formula V is illustrated by the following reaction scheme:

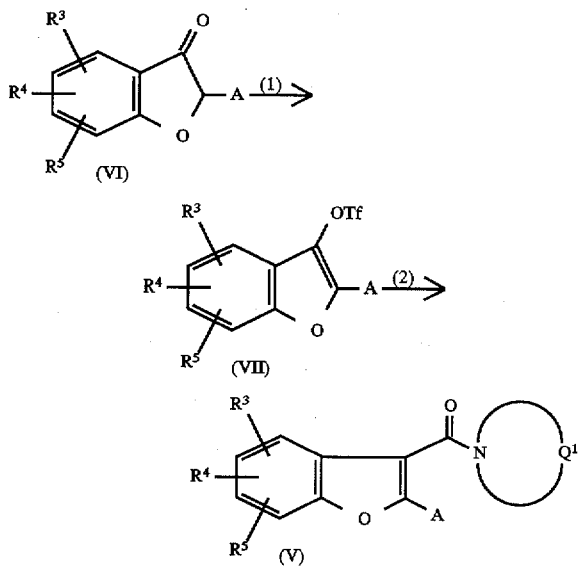

in which A, $R^3$, $R^4$, $R^5$ and $Q^1$ are as defined above; and Tf is an abbreviation for triflyl (trifluoro-methanesulfonyl).

In step (1), the cyclic ketone of formula VI is reacted with triflic anhydride ($Tf_2O$), advantageously in the presence of a base such as N,N-diisopropylethylamine or di-tert-butylpyridine, and suitably in an inert solvent such as dichloromethane. The intermediate of formula VII thereby obtained is then reacted in step (2) with carbon monoxide and the appropriate compound of formula IV as defined above, the reaction being suitably mediated by palladium(II) acetate in the presence of 1,1'-bis(diphenylphosphino) ferrocene (DPPF).

Where they are not commercially available, the starting materials of formula III, IV and VI may be prepared by procedures analogous to those described in the accompanying Examples, or by standard methods well known from the art. For example, a compound of formula III wherein L is halo may be prepared as described in the Examples, or by the method described in J. Heterocycl. Chem., 1978, 15, 481. In particular, the compounds of formula III above wherein L is chloro may be prepared by firstly reacting the appropriate compound of formula VII as defined above with carbon monoxide and methanol, advantageously in the presence of palladium(II) acetate and DPPF. The resulting methyl ester derivative is then reduced, typically with diisobutylaluminium hydride (DIBAL), to the corresponding hydroxymethyl analogue, which in turn can be reacted with thionyl chloride to give the required chloro compound.

It will be appreciated that any compound of formula I initially obtained from any of the above processes may, where appropriate, subsequently be elaborated into a further desired compound of formula I using techniques known from the art.

Where the above-described processes for the preparation of the compounds of formula I give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The following Example illustrates the preparation of a specific methanesulfonate salt according to the invention.

The methanesulfonate salts according to this invention potently inhibit [$^3$H]-spiperone binding to human dopamine $D_4$ receptor subtypes expressed in clonal cell lines.

Moreover, these salts display a selective affinity for the $D_4$ subtype relative to the $D_2$ subtype.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The salt of the accompanying Example was tested in the above assay, and was found to possess a $K_i$ value for displacement of [$^3$H]-spiperone from the human dopamine $D_4$ receptor subtype of below 1.5 μM.

PREPARATION 1

(E)-3-[4-(2-Phenylethenyl)-1,2,3,6-tetrahydropyridin-1-yl]methylbenzo[b]furan

Step 1: Methyl benzo[b]furan-3-carboxylate

A mixture of benzo[b]furan-3-yl trifluoromethanesulfonate (5.00 g, 18.8 mmol), triethylamine (5.2 ml, 37.3 mmol), palladium (II) acetate (0.130 g, 0.579 mmol), 1,1'-bis(diphenylphosphino)ferrocene (0.628 g, 1.13 mmol), and methanol (17 ml) in dimethylformamide (40 ml) was purged with carbon monoxide for 20 minutes and stirred under a carbon monoxide balloon at 60° C. for 2.5 hours. The reaction mixture was allowed to cool, diluted with water (250 ml) and extracted with ethyl acetate (2×100 ml). The extracts were washed with 1M hydrochloric acid (100 ml) then saturated brine (100 ml), combined and dried (magnesium sulfate). The solvent was evaporated and the residue purified by flash chromatography, eluting with 5% ethyl acetate in petrol (60°–80° ) then 10% ethyl acetate in petrol (60°–80° ), to afford the title compound (2.65 g, 80%) as a pale yellow oil; $\delta_H$ (CDCl$_3$) 3.94 (3H, s, CO$_2$CH$_3$), 7.34–7.39 (2H, m, ArH), 7.53 (1H, m, ArH), 8.07 (1H, m, ArH), 8.26 (1H, s, 2-H).

Step 2: 3-Hydroxymethylbenzo[b]furan

Diisobutylaluminium hydride in toluene (1.5M, 16.8 ml, 25.2 mmol) was added dropwise to a solution of methyl benzo[b]furan-3-carboxylate (2.02 g, 11.5 mmol) in tetrahydrofuran (50 ml) at −75° C. The resulting solution was stirred at −75° C. for 30 minutes, the cooling bath removed and the mixture allowed to warm to room temperature. The reaction mixture was recooled to −40° C. and quenched by sequential addition of methanol (3 ml), water (1.5 ml) and 2M sodium hydroxide (1.5 ml). The mixture was allowed to warm up to produce a gel, which was filtered off and washed with dichloromethane (6×50 ml). The filtrate was evaporated to dryness, the residue redissolved in ether and the solution dried over magnesium sulfate. The solution was evaporated to afford the title compound (1.66 g, 98%) as an oil which crystallised on standing; $\delta_H$ (CDCl$_3$) 1.61 (1H, br s, OH), 4.85 (2H, s, CH$_2$OH), 7.25–7.35 (2H, m, ArH), 7.49 (1H, dd, J 7.8, 1.0Hz, ArH), 7.61 (1H, s, 2-H), 7.67 (1H, m, ArH).

Step 3: (E)-3-[4-(2-Phenylethenyl)-1,2,3,6-tetrahydropyridin-1-yl]methylbenzo[b]furan Thionyl chloride (0.25 ml, 3.4 mmol) was added to a solution of 3-hydroxymethylbenzo[b]furan (0.4515 g, 3.05 mmol) in anhydrous ether (10 ml), the mixture was stirred at room temperature for 2.5 hours and evaporated to dryness. The residue was dissolved in anhydrous dimethylformamide (10 ml), potassium carbonate (1.05 g, 7.60 mmol) and (E)-4-(2-phenylethenyl)-1,2,3,6-tetrahydropyridine (0.68 g, 3.67 mmol) was added and the mixture stirred at room temperature, under nitrogen, overnight (20 hours). The reaction mixture was poured into water (100 ml) and extracted with ethyl acetate (2×50 ml). The extracts were washed with saturated brine (50 ml), combined and dried (magnesium sulfate). The residue after evaporation of the solvent was purified by flash chromatography, eluting with 20% then 25% ethyl acetate/petrol (60°–80°), to afford the title compound (0.4734 g, 49%). Recrystallisation from ethyl acetate/petrol (60°–80°) gave pale yellow needles, m.p. 122°–123° C.; (Found: C, 8.29; H, 6.58; N, 4.36. C$_{22}$H$_{21}$NO.0.1H$_2$O requires C, 83.30; H, 6.74; N, 4.42%); $\delta_H$ (CDCl$_3$) 2.43 (2H, br s, tetrahydropyridinyl CH$_2$), 2.73 (2H, t, J 5.7Hz, tetrahydropyridinyl CH$_2$), 3.21 (2H, d, J 2.7Hz, tetrahydropyridinyl CH$_2$), 3.76 (2H, s, ArCH$_2$N), 5.82 (1H, br s, tetrahydropyridinyl CH), 6.44 (1H, d, J 16.1Hz, CH=CHPh), 6.79 (1H, d, J 16.1Hz, CH=CHPh), 7.17–7.32 (5H, m, ArH), 7.39 (2H, m, ArH), 7.48 (1H, m, ArH), 7.58 (1H, s, 2-H), 7.73 (1H, m, ArH); m/z (ES$^+$) 316 (M+1)$^+$.

EXAMPLE 1

(E)-3-[4-(2-Phenylethenyl)-1,2,3,6-tetrahydropyridin-1-yl]methylbenzo[b]furan methanesulfonate salt Methanesulfonic acid (0.14 ml, 2.16 mmol) was added to a solution of (E)-3-[4-(2-phenylethenyl)-1,2,3,6-tetrahydropyridin-1-yl]methylbenzo[b]furan (0.6817 g, 2.16 mmol) in ethyl acetate (15 ml) to give a white precipitate. The solid was collected under suction, washed with ethyl acetate and recrystallised from 2-propanol to afford the title compound (0.6979 g, 78%), m.p. 216.5°–218° C. (dec.); (Found: C, 67.04; H, 6.08; N, 3.44. C$_{23}$H$_{25}$NO$_4$S requires C, 67.13; H, 6.13; N, 3.40%); $\delta_H$ (500MHz, DMSO-d$_6$) 2.43 (3H, s, CH$_3$SO$_3$), 2.66 (2H, m, tetrahydropyridinyl CH$_2$), 3.29 (1H, m, tetrahydropyridinyl CH$_2$), 3.71 (1H, m, tetrahydropyridinyl CH$_2$), 3.90 (2H, m, tetrahydropyridinyl CH$_2$), 4.60 (2H, br s, ArCH$_2$N), 5.90 (1H, s, tetrahyropyridinyl CH), 6.61 (1H, d, J 16.3Hz, CH=CHPh), 6.97 (1H, d, J 16.3Hz, CH=CHPh), 7.24 (1H, t, J 7.3Hz, ArH), 7.31–7.42 (4H, m, ArH), 7.50 (2H, d, J 7.5Hz, ArH), 7.66 (1H, d, J 7.7Hz, ArH), 7.93 (1H, d, J 7.2Hz, ArH), 8.25 (1H, s, 2-H), 10.01 (1H, br s, NH⁺); m/z (ES⁺) 316 [(M+H)⁺].

We claim:

1. The methanesulfonate (mesylate) salt of a compound of formula I:

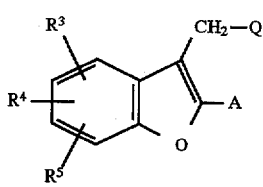
(I)

wherein

A represents hydrogen, $C_{1-6}$ alkyl, $C_{1-6}$ alkoxy, halogen, cyano or trifluoromethyl;

Q represents a moiety of formula Qa, Qb, Qc or Qd:

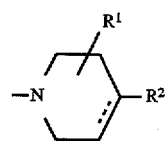
(Qa)

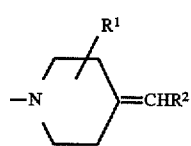
(Qb)

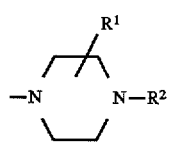
(Qc)

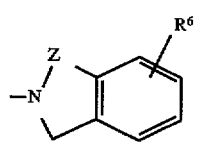
(Qd)

in which the broken line represents an optional chemical bond;

$R^1$ represents hydrogen, or an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^2$ represents an optionally substituted $C_{1-6}$ alkyl, $C_{1-6}$ alkoxy, $C_{2-6}$ alkenyl, $C_{2-6}$ alkynyl, aryl, aryl($C_{1-6}$) alkyl, aryloxy($C_{1-6}$)alkyl, aryl($C_{1-6}$)alkoxy, aryl($C_{2-6}$) alkenyl, aryl($C_{2-6}$)alkynyl, $C_{3-7}$ heterocycloalkyl ($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$;

Z represents —CH$_2$— or —CH$_2$CH$_2$—;

$R^6$ represents hydrogen or halogen, or an optionally substituted $C_{1-6}$ alkyl, $C_{1-6}$ alkoxy, aryl, aryloxy, aryl ($C_{1-6}$)alkyl, aryl($C_{1-6}$)alkoxy or heteroaryl group; and $R^a$ and $R^b$ independently represent hydrogen, hydrocarbon or a heterocyclic group.

2. The mesylate salt as claimed in claim 1 wherein A represents hydrogen.

3. The mesylate salt as claimed in claim 1 wherein Q represents a moiety of formula Qa.

4. The mesylate salt as claimed in claim 1 wherein $R^1$ represents hydrogen.

5. The mesylate salt as claimed in claim 1 wherein $R^2$ represents phenylethenyl.

6. The mesylate salt as claimed in claim 5 wherein the phenylethenyl group $R^2$ is in the (E) geometrical isomeric form.

7. The mesylate salt as claimed in claim 1 wherein $R^3$, $R^4$ and $R^5$ each represents hydrogen.

8. The methanesulfonate salt of a compound of formula IIA:

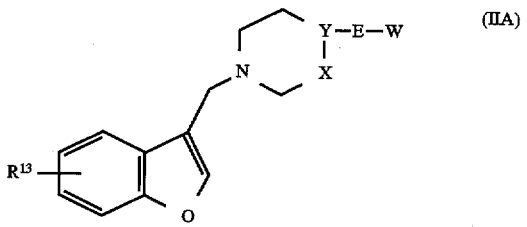
(IIA)

wherein

E represents —(CH$_2$)$_n$—, —CH=CH— or —C≡C—; n is zero, 1, 2 or 3;

—X—Y— represents —CH$_2$—CH—, —CH=C— or —CH$_2$—N—;

W represents a group of formula (i), (ii), (iii), (iv), (v) or (vi):

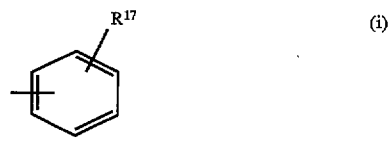
(i)

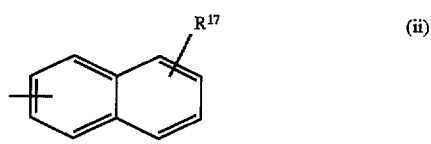
(ii)

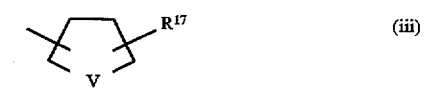
(iii)

(iv)

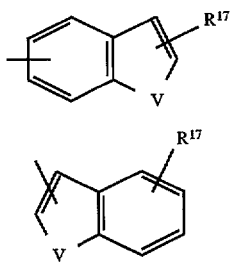

in which V represents oxygen, sulfur or NH; and $R^{13}$ and $R^{17}$ independently represent hydrogen, halogen, cyano, nitro, trifluoromethyl, amine, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl.

9. The mesylate salt as claimed in claim 8 wherein $R^{13}$ represents hydrogen.

10. The mesylate salt as claimed in claim 8 wherein $R^{17}$ represents hydrogen.

11. The mesylate salt as claimed in claim 8 wherein E represents —CH=CH—, —X—Y— represents —CH=C—, W represents a group of formula (i), and $R^{13}$ and $R^{17}$ are both hydrogen.

12. The mesylate salt as claimed in claim 11 wherein the moiety E is in the (E) geometrical isomeric configuration.

13. The methanesulfonate salt of a compound of formula IIB:

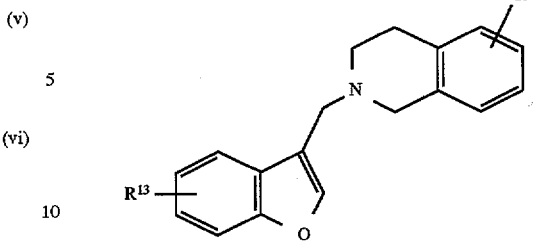

wherein $R^{13}$ is as defined in claim 8; and $R^{16}$ represents hydrogen, halogen, $C_{1-6}$ alkyl, $C_{1-6}$ alkoxy, aryl, haloaryl, aryloxy, axyl($C_{1-6}$)alkyl, aryl ($C_{1-6}$)alkoxy or heteroaryl.

14. The methanesulfonate salt of (E)-3-[4-(2-phenylethenyl)-1,2,3,6-tetrahydropyridin-1-yl]methylbenzo[b]furan.

15. A pharmaceutical composition comprising the methanesulfonate salt of a compound of formula I as defined in claim 1 in association with a pharmaceutically acceptable carrier.

16. A method for the treatment and/or prevention of psychotic disorders, which comprises administering to a patient in need of such treatment an effective amount of the methanesulfonate salt of a compound of formula I as defined in claim 1.

* * * * *